(12) United States Patent
Melkent et al.

(10) Patent No.: US 8,465,547 B2
(45) Date of Patent: Jun. 18, 2013

(54) MODULAR INTERBODY DEVICES AND METHODS OF USE

(75) Inventors: Anthony J. Melkent, Memphis, TN (US); William David Armstrong, Memphis, TN (US); Lindsey G. Waugh, Memphis, TN (US); Frank J. Schwab, New York, NY (US); Christopher I. Shaffrey, Charolettesville, VA (US); Brian Bulter, Atoka, TN (US); Stanley Palmatier, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 587 days.

(21) Appl. No.: 12/694,778

(22) Filed: Jan. 27, 2010

(65) Prior Publication Data

US 2011/0184522 A1 Jul. 28, 2011

(51) Int. Cl.
*A61F 2/44* (2006.01)
*A61F 2/46* (2006.01)
*A61B 17/88* (2006.01)
*A61B 17/90* (2006.01)
*A61B 17/60* (2006.01)

(52) U.S. Cl.
USPC .............................. 623/17.16; 606/90; 606/99

(58) Field of Classification Search
USPC ........................ 623/17.11–17.16; 606/90, 99
See application file for complete search history.

(56) References Cited

U.S. PATENT DOCUMENTS

| | | | | |
|---|---|---|---|---|
| 2004/0030387 | A1* | 2/2004 | Landry et al. | 623/16.11 |
| 2004/0220582 | A1* | 11/2004 | Keller | 606/99 |
| 2010/0010494 | A1* | 1/2010 | Quirno | 606/90 |

* cited by examiner

*Primary Examiner* — Michael T Schaper

(57) ABSTRACT

Methods and devices for spacing vertebral members using modular intervertebral devices and insertion tools. The devices may include opposing first and second endplates, and an intermediate member configured to fit between and support the endplates. The insertion tool may include an elongated handle and a distracter. A method of inserting the device using the tool may include inserting the endplates positioned on opposing sides of the handle into the intervertebral space and positioning the endplates in the intervertebral space relative to first and second vertebral members. The method may include deploying the distracter and increasing a distance between the endplates. Another step may include inserting the intermediate member into the intervertebral space and between the endplates and supporting the endplates with the intermediate member. The insertion tool may then be removed from the intervertebral space.

21 Claims, 17 Drawing Sheets

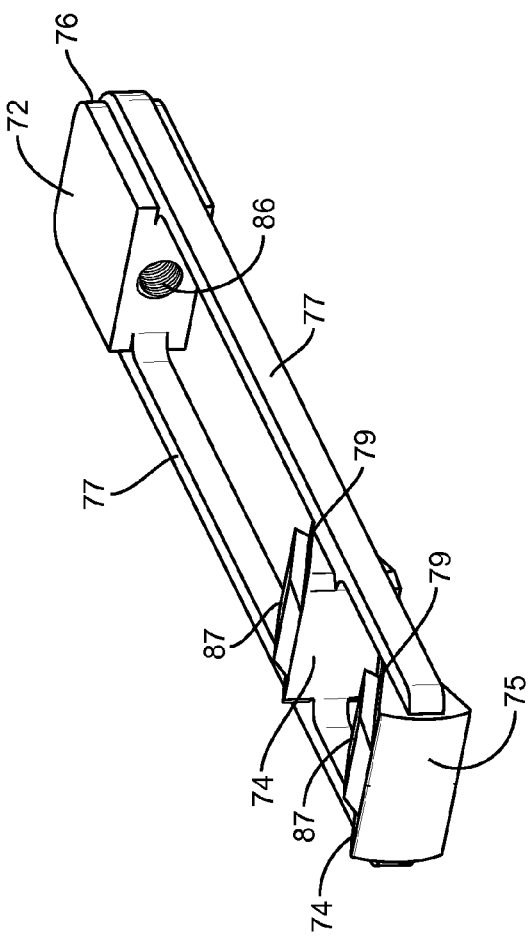
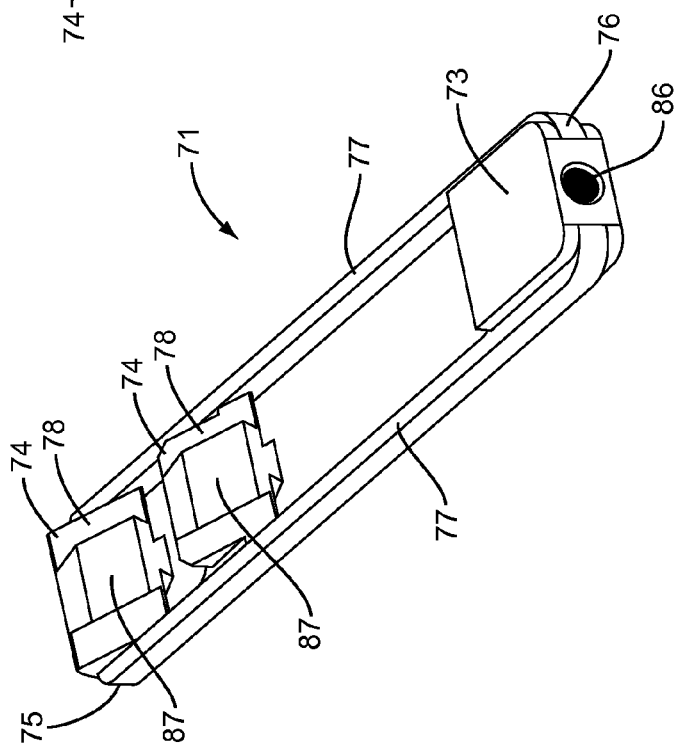
FIG. 11
FIG. 10

MODULAR INTERBODY DEVICES AND METHODS OF USE

BACKGROUND

The present invention relates generally to vertebral implants, and more particularly to modular interbody devices and insertion instruments.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage or degeneration to the intervertebral discs and vertebral members can lead to pain, neurological deficit, and/or loss of motion and disability.

Various procedures include replacing the entirety or a section of a vertebral member, the entirety or a section of an intervertebral disc, or both. One or more replacement implants may be inserted to replace the damaged vertebral members and/or discs. The implants may further include bone growth material to facilitate fusion of the implant to one or both adjacent vertebral members. The implant may provide for housing the bone growth material. Instruments may be configured for inserting the implants into the intervertebral space. The instruments may provide for accurately placing the implants within the space.

SUMMARY

The present application is directed to modular intervertebral devices, insertion tools, and methods of insertion of the modular interbody devices into an intervertebral space between first and second vertebral members. The devices may include opposing first and second endplates, and an intermediate member configured to fit between and support the endplates. The insertion tool may include an elongated handle and a distracter. A method of inserting the device may include inserting the endplates positioned on opposing sides of the handle into the intervertebral space and positioning the endplates in the intervertebral space relative to the first and second vertebral members. The method may include deploying the distracter and increasing a distance between the endplates. Another step may include inserting the intermediate member into the intervertebral space and between the endplates and supporting the endplates with the intermediate member. The insertion tool may then be removed from the intervertebral space.

The various aspects of the various embodiments may be used alone or in any combination, as is desired.

BRIEF DESCRIPTION OF THE DRAWINGS

FIG. 10 is a perspective view of an inferior side of a sled according to one embodiment.

FIG. 11 is a perspective view of a superior side of a sled according to one embodiment.

DETAILED DESCRIPTION

Figure 1:
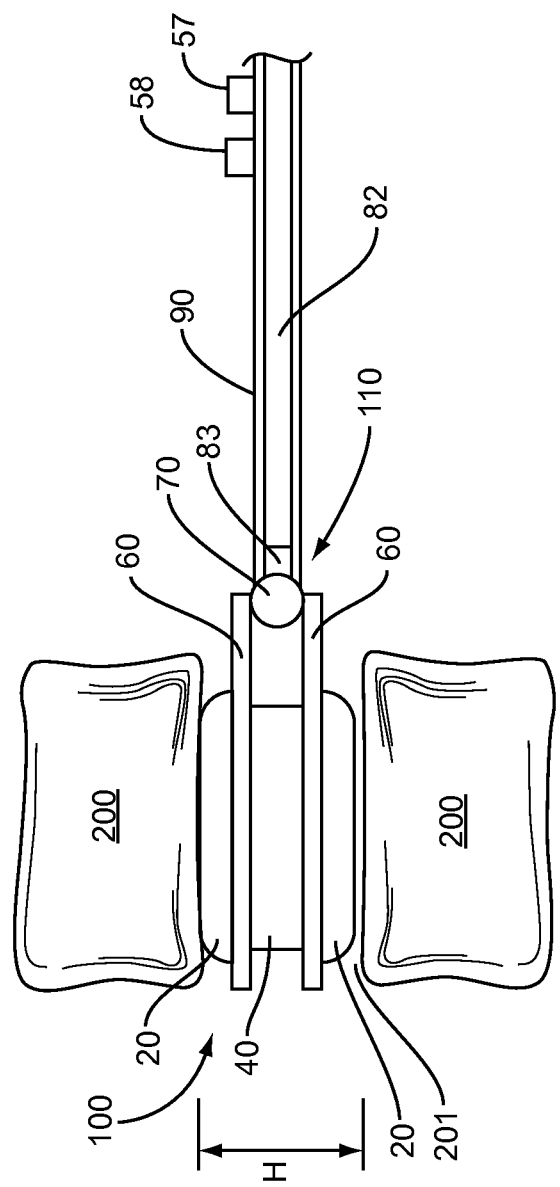
FIG. 1 is a schematic diagram of an interbody device and an insertion tool according to one embodiment.

The present application is directed to modular interbody devices, insertion instruments, and methods of using the devices and instruments. FIG. 1 schematically illustrates an interbody device 100 operatively connected to an insertion tool 110 and positioned within an intervertebral space 201 formed between vertebral members 200. The interbody device 100 includes endplates 20 and an intermediate section 40. The endplates 20 and intermediate section 40 may include engagement features that mate together. The insertion tool 110 includes connectors 60 for connecting with the endplates 20, a distracter 70, and a handle 90.

During use, the endplates 20 are positioned on the connectors 60. The distracter 70 is positioned in a retracted orientation with a reduced height H measured between the endplates 20. The surgeon then manipulates the handle to insert the endplates 20 and at least a section of the connectors 60 and the distracter 70 into the intervertebral space 201. The interbody device 100 and insertion tool 110 may be configured for insertion into the intervertebral space 201 from different approaches, such as anterior, posterior, lateral, and oblique approaches. The endplates 20 establish the footprint of the interbody device 100 once inserted into the intervertebral space 201. After insertion, the distracter 70 separates the connectors 60 and connected endplates 20 thereby increasing the height H of the device 100 and distracting the vertebral members 200. The surgeon may be able to customize the height H of the interbody device 100 through feedback received during the distraction. This may include tactile feedback received by the surgeon during the distraction and/or from monitoring a force gauge 58 associated with the insertion tool 110. The gauge 58 may be a torque meter or like sensing mechanism to indicate when a particular torque (and therefore a particular distraction force) has been achieved. A second gauge 57 may also be a height meter to indicate the height H of the device 100. After the distraction, the intermediate section 40 is inserted into the intervertebral space 201 and connected to the endplates 20. The intermediate section 40 maintains the desired height H and orientation of the endplates 20 such that the insertion tool 110 can be removed from the device 100 and intervertebral space 201. The gauges 57, 58 may be separate as schematically illustrated in FIG. 1, or may be combined in a single unit.

Figure 2:
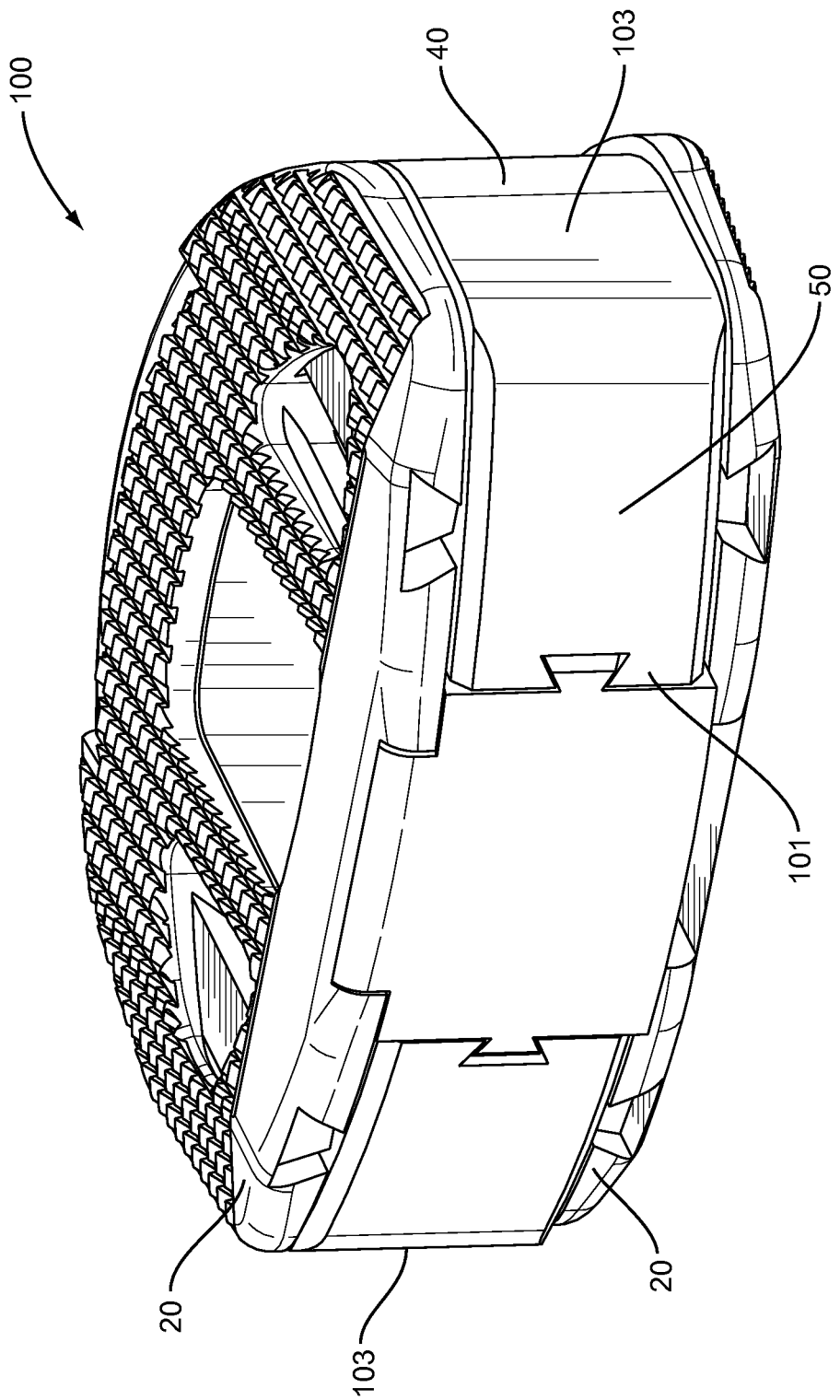
FIG. 2 is a perspective posterior view of a device according to one embodiment.
Figure 3:
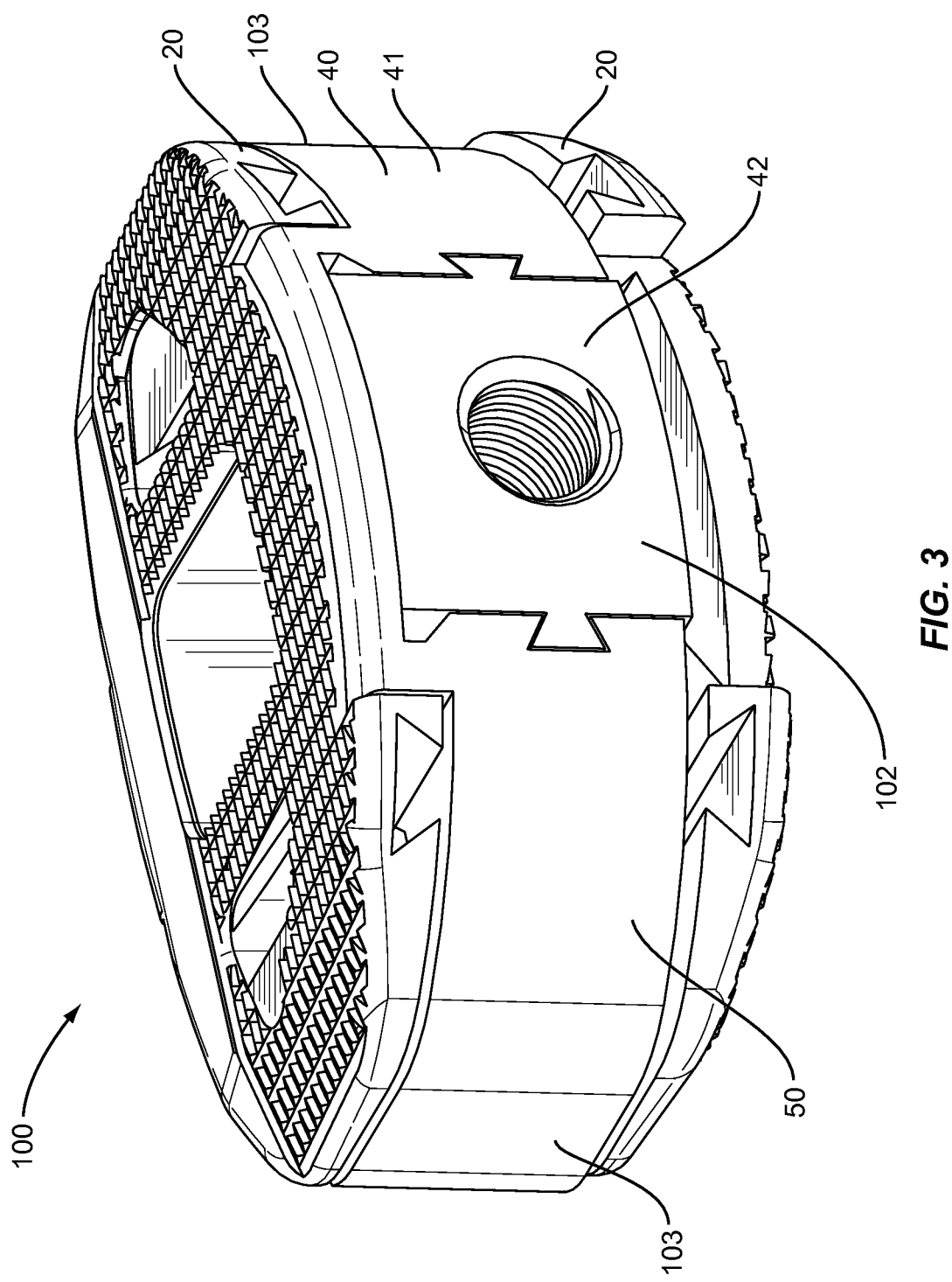
FIG. 3 is a perspective anterior view of a device according to one embodiment.

FIGS. 2 and 3 illustrate a device 100 that includes a pair of endplates 20 separated by an intermediate section 40. The device 100 includes a posterior side 101, anterior side 102, and lateral sides 103. The superior and inferior sides are formed by the endplates 20. The device 100 may include various heights measured between the endplates 20, shapes, and configurations depending upon the anatomy of the patient and the vertebral level at which it will be inserted into the intervertebral space 201.

The endplates 20 are positioned on the superior and inferior sides of the device 100. Each endplate 20 includes an exterior side 21 that faces outward and contacts against one of the vertebral members 200, and an interior side 22 that faces inward and connects with the intermediate section 40. The inferior and exterior endplates 20 of a device 100 may be the same or may include different shapes, sizes, and configurations.

Figure 4:
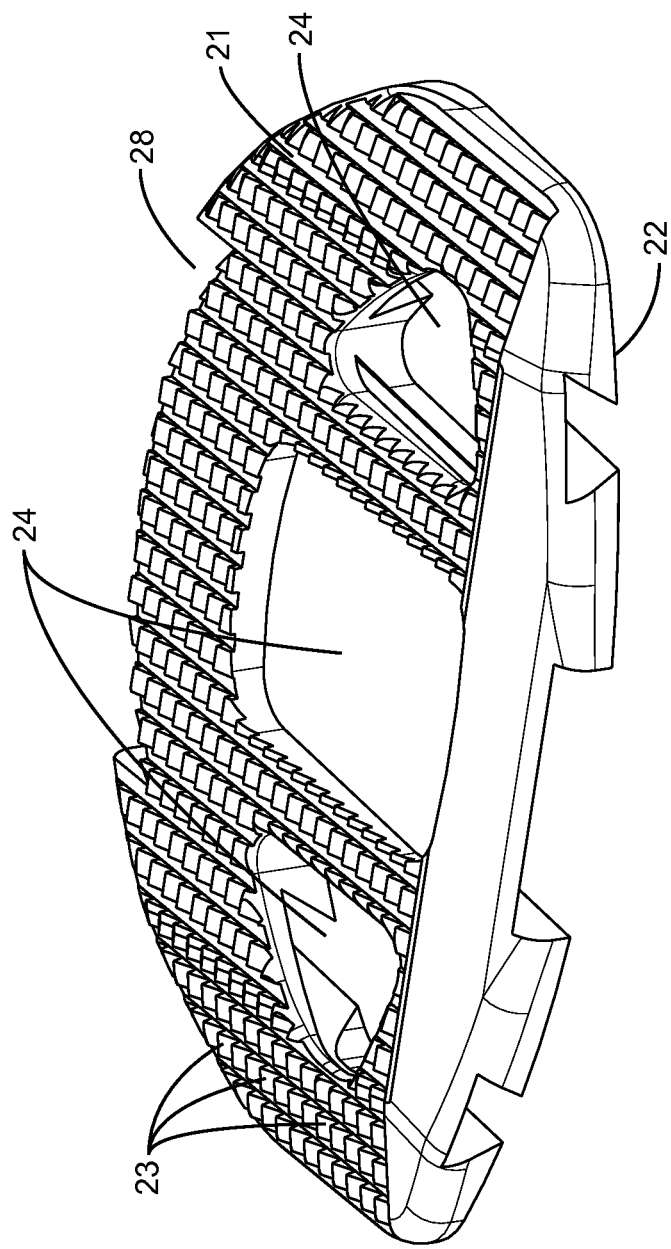
FIG. 4 is perspective view of an exterior side of an endplate according to one embodiment.

FIG. 4 illustrates an exterior side 21 of an endplate 20. Teeth 23 may be positioned across the entirety or a limited section of the exterior side 21. One or more apertures 24 may extend through the endplate 20. The apertures 24 may facilitate fusion of the device 100 with the vertebral member 200 as will be explained in more detail below. A recess 28 may be formed on one side of the endplate 20 to receive a section of the intermediate section 40.

Figure 5:
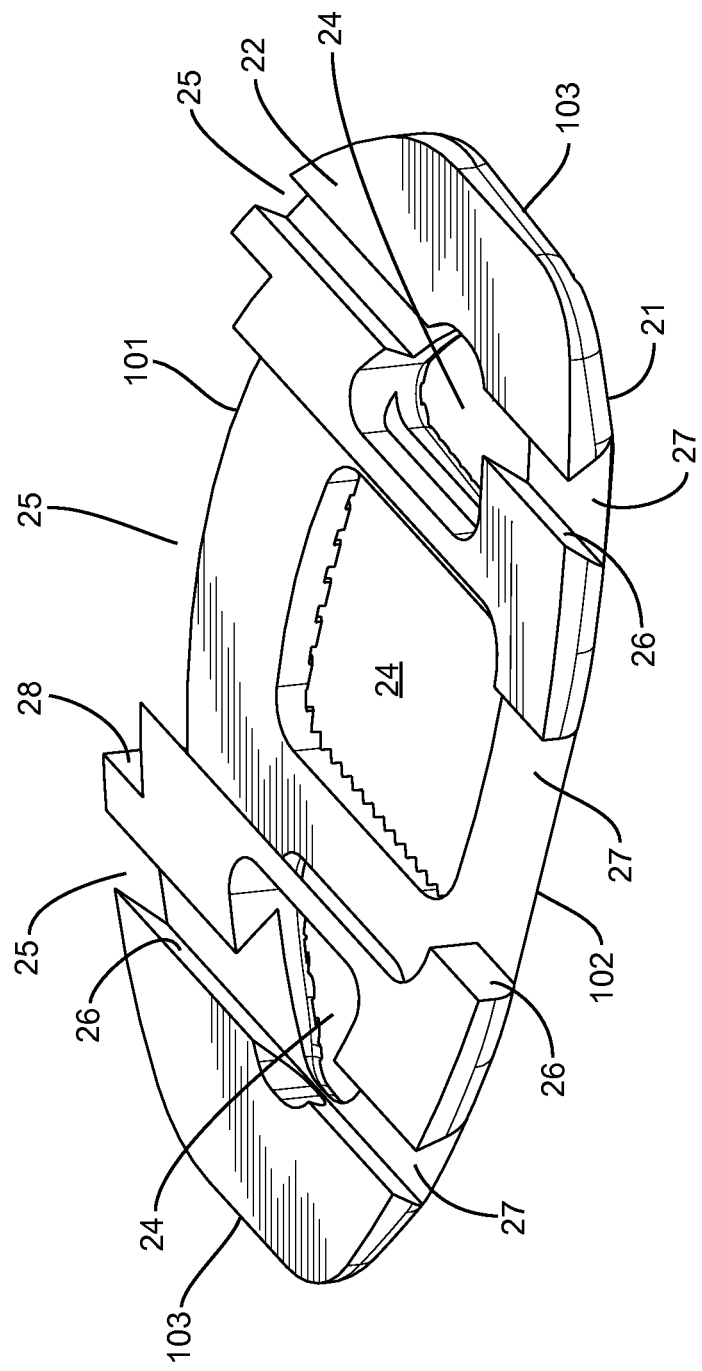
FIG. 5 is perspective view of an interior side of an endplate according to one embodiment.

An interior side 22 of an endplate 20 is illustrated in FIG. 5. One or more slots 25 may extend across the interior side 22. The slots 25 include opposing sidewalls 26 and a bottom side 27. The sidewalls 26 may be slanted forming a dovetailed configuration with a narrow opening that increases in width towards the bottom side 27. The slots 25 may be straight as illustrated in FIG. 5 with an axis extending along the length. The alignment of the slots 25 is dependent upon the insertion approach for inserting the device 100 into the intervertebral space 201. FIG. 5 includes each slot 25 arranged in a posterior-anterior alignment and each extends across the entire endplate 20 and is open on the posterior side 101 and anterior side 102. In another embodiment (not illustrated), the slots 25 are arranged in a lateral alignment that extend between the lateral sides 103 and provide for insertion using a lateral approach. Other embodiments feature oblique and posterior orientations of the slots 25. Various slot alignments may be structured in the interior side 22 depending upon the desired approach angle.

Each of the slots 25 includes an elongated shape that may extend across the entire endplate 20, or a limited section of the endplate 20. FIG. 5 includes the slots 25 extending across the entire interior side 22. Slots 25 may also include a closed back end such that the slots 25 do not extend across the entire side. Further, the dimensions of the slots 25 may vary along their length.

FIGS. 2 and 3 include each of the endplates 20 being flat with a substantially constant thickness between the exterior and interior sides 21, 22. The endplates 20 may also include a wedge shape with a varying thickness between the sides 21, 22. The endplates 20 may include a varying thickness in a single plane, or in multiple planes. The angular orientations of the endplates 20 accommodate variations in the orientations of the vertebral members 200 at different vertebral levels, such as the variations caused by lordosis and kyphosis. Further, the exterior surfaces 21 may include other shapes and configurations, such as convex and concave sections, to accommodate and engage with the vertebral members 200.

The intermediate section 40 of the device 100 may be constructed from one or more members. FIG. 3 includes a device 100 with the intermediate section 40 constructed from a first member 41 and a second member 42. The members 41, 42 engage together and are positioned between the endplates 20. Other embodiments feature a single intermediate section 40 (i.e., just a first member 41) positioned between the endplates 20.

Figure 6:
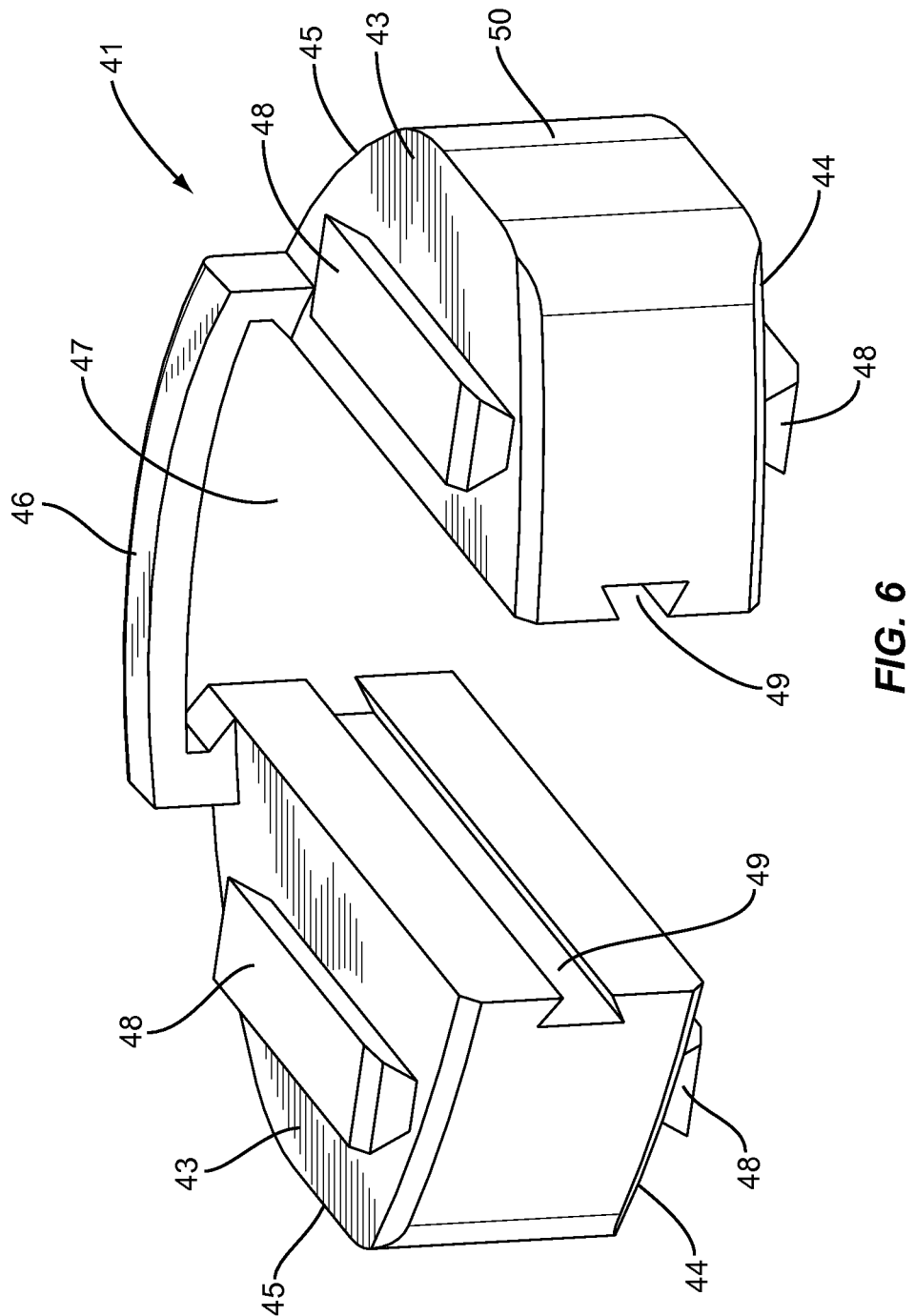
FIG. 6 is a perspective view of a first member of an intermediate section according to one embodiment.

FIG. 6 illustrates a first member 41 that includes a pair of sections 45 that are spaced apart by a gap 47 and connected by a connector 46. The sections 45 may include the same or different shapes, sizes, and configurations. FIG. 6 includes the sections 45 being substantially the same. Each section 45 includes a superior side 43 and an opposing inferior side 44. One or more projections 48 may extend outward from the superior and inferior sides 43, 44. FIG. 6 illustrates two projections 48 extending outward from each of the sides 43, 44 with opposing projections 48 extending outward from each of the sections 45. The projections 48 are configured to mate with the slots 25 on the interior side 22 of the endplates 20. The projections 48 may include an elongated shape that is straight and includes an axis. The projections 48 may each include the same or different shapes, sizes, and configurations. In one embodiment, the projections include a dovetail configuration that is wider at an outer end and narrows downward as illustrated in FIG. 6.

A sidewall 50 extends between the superior and inferior sides 43, 44. An exterior section of the sidewall 50 is exposed on the exterior of the device 100 as illustrated in FIGS. 2 and 3. Interior sections of the sidewall 50 may include one or more slots 49. The slots 49 may include opposing sidewalls and a bottom wall similar to the slots 25 in the endplates 20. The slots 49 may also include a dovetail configuration with a tapering width as illustrated in FIG. 6.

The connector 46 extends between and connects the sections 45. The connector 46 may be positioned on an edge of the first member 41 to fit within the recess 28 in the endplate 20. The connector 46 may also extend outward beyond the sections 45. As illustrated in FIG. 6, the connector 46 extends outward beyond the superior side 43.

Figure 7:
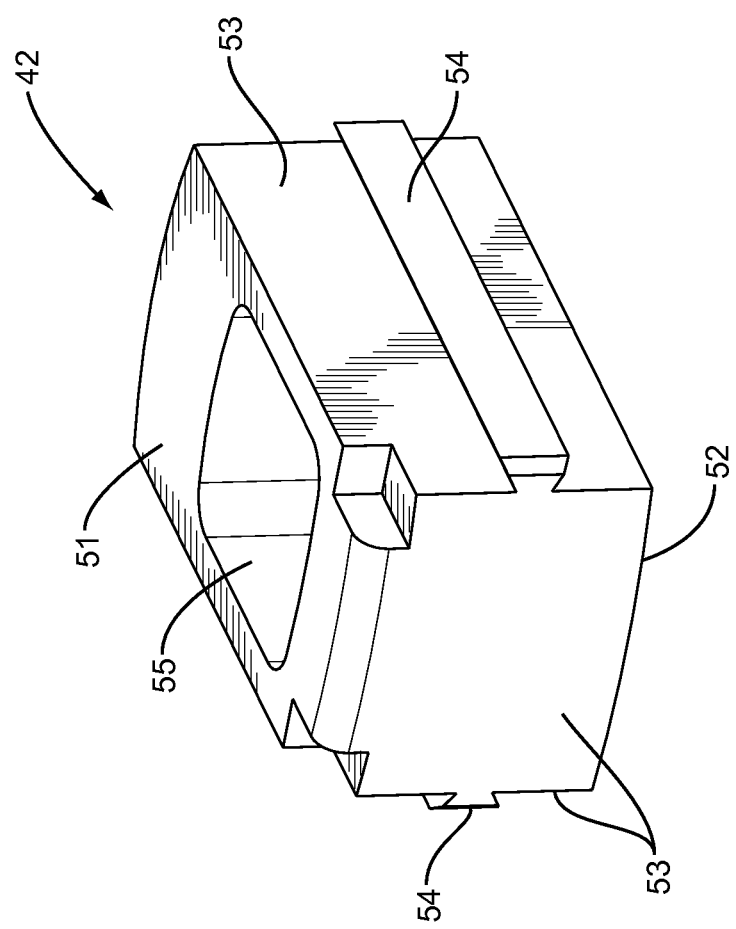
FIG. 7 is a perspective view of a second member of an intermediate section according to one embodiment.

The intermediate section 40 may also be constructed from a second member 42 as illustrated in FIG. 7. The second member 42 is sized and configured to fit with the gap 47 of the first member 41. The second member 42 may include a superior side 51 and an inferior side 52. A sidewall 53 extends between the sides 51, 52. One or more projections 54 may extend outward from the sidewall 53 to engage with slots 49 in the first member 41. FIG. 7 specifically includes a pair of projections 54 on opposing sections of the sidewall 53 that engage with the slots 49 on the interior sections of the sidewall 50. The projections 54 may be the same or different, and may include various shapes, sizes, and configurations. FIG. 7 includes each of the projections 54 with a dovetail shape. The projections 54 are straight with a longitudinal axis that aligns with the longitudinal axis of the slot 49 on the first member 41.

A receptacle 55 is positioned in the second member 42 and may be configured to hold bone-growth material that facilitates fusion of the device 100 with the vertebral members 200. The receptacle 55 may extend through the entirety of the second member 42, or may include a limited depth and be open to just one of the inferior and superior sides. The receptacle 55 may align with one or more of the apertures 24 in the endplates 20 when the second member 42 is positioned in the device 100.

The various engagement features such as the slots and projections of the different elements are each configured to connect the elements together. The engagement features are aligned in a common direction depending upon the approach angle. Further, some or all of the engagement features may include an elongated, straight shape with a longitudinal axis. The engagement features of FIGS. 2-7 are each arranged in an anterior-posterior alignment for insertion of the device 100 using an anterior approach or a posterior approach. The engagement features may also be arranged in different alignments to accommodate different approaches. The various engagement members may also include locking features that lock the elements together once they have been arranged together. Examples of locking features include corresponding ball-and-detents, locking flanges, tabs, taper-fits, snap fits, and the like.

Figure 8:
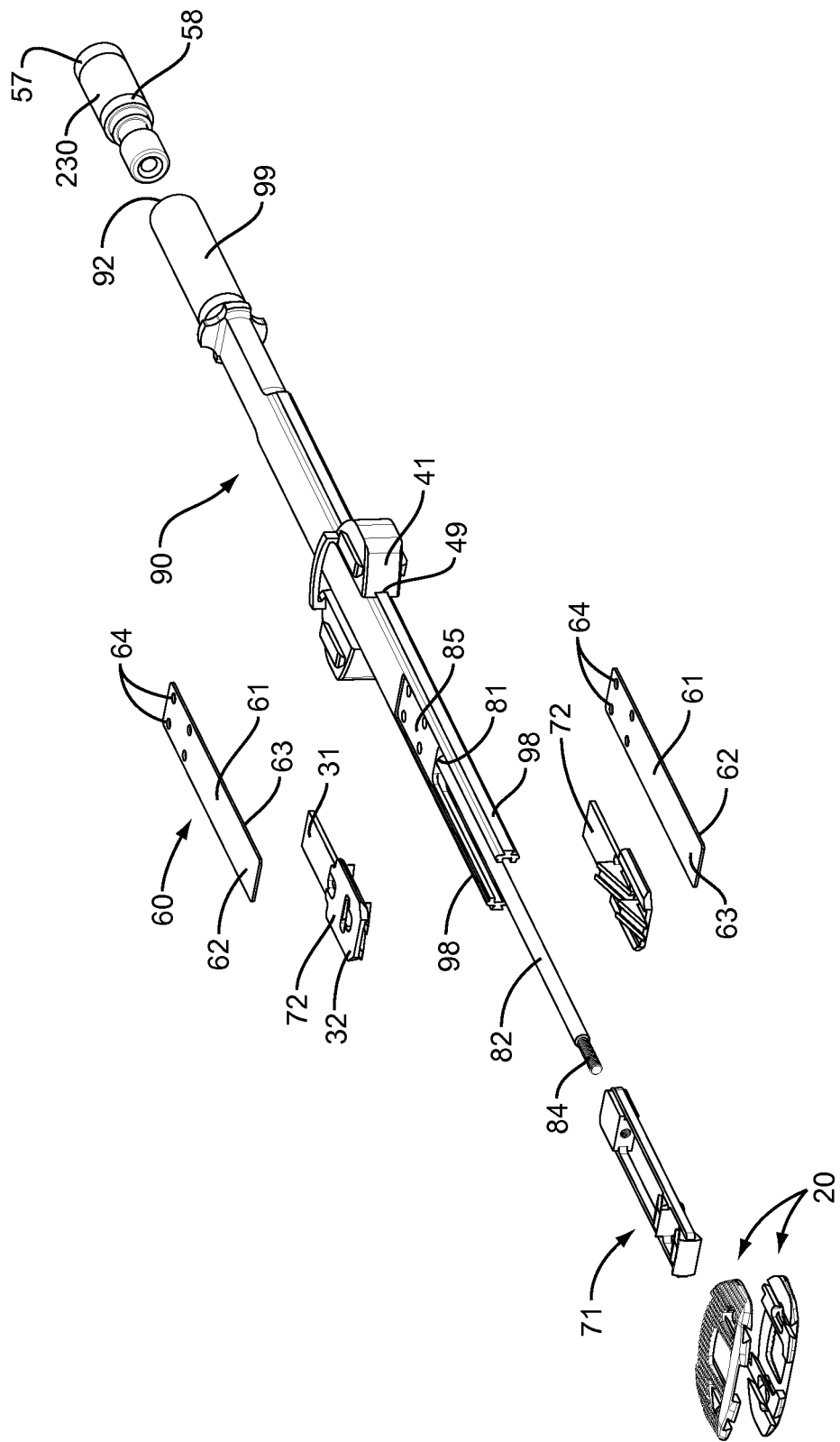
FIG. 8 is an exploded perspective view of an insertion tool according to one embodiment.

The insertion tool 110 may position the device 10 within the intervertebral space 201, distract the vertebral members 200, and increase the height H of the device 100. FIG. 8 illustrates an exploded view of an insertion tool 110. Endplates 20 and a first member 41 are also included for reference. The tool 110 has an elongated shape and includes a handle 90, connectors 60 including first and second ribbons 61, and a distracter 70 including a sled 71 and opposing supports 72.

Figure 9:
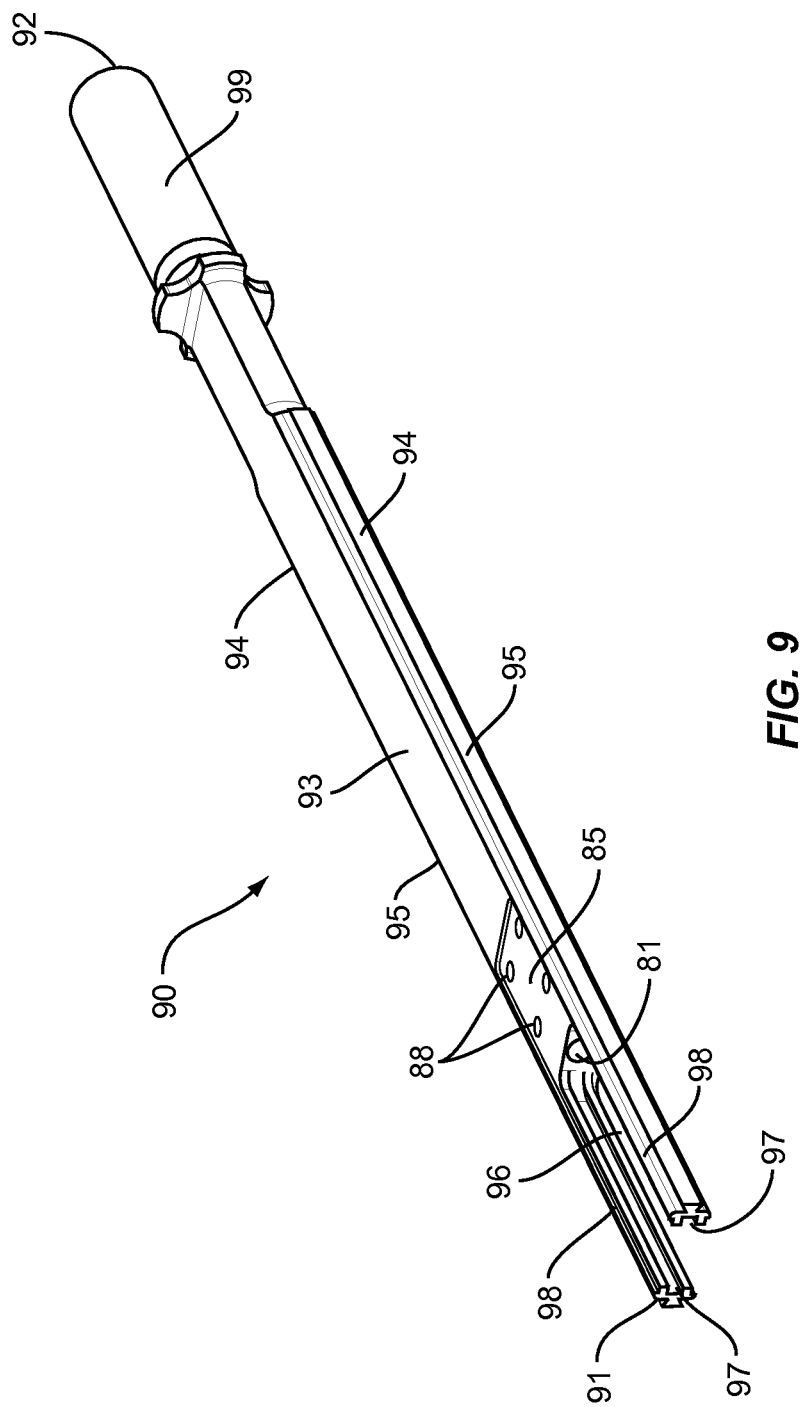
FIG. 9 is a perspective view of a handle of an insertion tool according to one embodiment.

FIG. 9 illustrates a handle 90 with an elongated body 93 extending between a distal end 91 and a proximal end 92. A longitudinal axis extends along the length and runs through the distal and proximal ends 91, 92. The handle 90 is substantially straight, although sections of the body 93 may also be curved to facilitate insertion of the device 100 into the intervertebral space 201 and/or distraction of the vertebral members 200 and an increase in the device height H. The distal end 91 includes a pair of fingers 98 that are spaced apart and form a pocket 96. The pocket 96 may extend inward from the distal end 91 an amount to receive the sled 71. Slots 97 may extend into the fingers 98 from the pocket 96 to engage with the sled 71. The slots 97 may be the same as slots 49 on the first member 41. In one embodiment, the slots 97 include a dovetailed shape for the sled to move along the length of the pocket 96 and remain connected to the handle 90. Recesses 85 may be positioned within opposing sides of the body 93 at the pocket 96 to receive the ribbons 61. Apertures 88 may further be positioned in the recesses.

Projections 95 may extend outward from sides 94 of the body 93 to engage with the slots 49 on the interior sides of the first member 41. The projections 95 may include opposing sidewalls and a top wall similar to the projections 48 of the first member 41. The projections 95 may further include a dovetailed configuration with a wider exterior and narrow neck to engage with the first member 41. This configuration allows the first member 41 to slide along the length while remaining connected to the handle 90. The projections 95 are positioned at the distal end 91 and extend inward along the length of the body 93. FIG. 9 includes the projections 95 extending along more than 75% of the body length. This length provides for the first member 41 to be loaded onto the distal end 91 and slid along the length and away from the distracter 70 and connectors 60.

An interior channel 81 extends through at least a portion of the body 93. As illustrated in FIGS. 8 and 9, the channel 81 exits into the pocket 96 towards the distal end. The channel 81 extends along the body 93 to the proximal end 92. An elongated member 82 (FIG. 1) extends through the channel 81 and is accessible at the proximal end 92. The distal end of the member 82 may be threaded, or may include a connection feature 83 to engage with a screw 84. The connection feature 83 may include a variety of structures to engage with the head of the screw 84, such as a socket receptacle, and a Philips or flathead projection.

The proximal end 92 includes a gripping surface 99 to facilitate manipulating the tool 110 during the insertion process. The proximal end 92 is also configured to apply a translation force to the member 82. In one embodiment, the proximal end 92 is configured to attach to a tool that applies a force to the member 82.

The ribbons 61 are positioned on opposing sides of the handle 90 to connect to the endplates 20. The ribbons 61 may include the same or different shapes, size, and structure. As illustrated in FIG. 8, the ribbons 61 include an interior side 63 that faces towards the handle 90 and an opposing exterior side 62. The ribbons 61 include a thickness measured between the sides 62, 63 that is relatively thin. The thickness may be uniform throughout the plate 61, or may vary. The ribbons 61 may be constructed from materials such as metals, plastics, and polymers. The thickness and the material may cause the ribbons 61 to flex during the insertion process. The ribbons 61 may include a shape that corresponds with the recesses 85 in the handle 90 for the ribbons 61 to seat within the recesses 85 when the instrument 110 is in a retracted orientation. The ribbons 61 may include one or more apertures 64 that align with corresponding apertures 88 in the handle 90. Connectors extend through the apertures 64, 88 to connect the ribbons 61 to the handle 90.

The distracter 70 includes the sled 71 and opposing supports 72. The sled 71 is positioned within the pocket 96 and moves along the length of the pocket 96. This movement engages inclined surfaces on the sled 71 with corresponding incline surfaces on the supports 72 to increase the height H of the device 100 and also to distract the vertebral members 200.

A sled 71 is illustrated in FIGS. 10 and 11. The sled 71 has an elongated shape that extends between a distal end 75 and a proximal end 76. The distal end 75 may include a rounded or tapered shape to facilitate insertion into the intervertebral space 201. The sled 71 includes a superior side 79 that faces towards the superior endplate 20, and an inferior side 78 that faces towards the inferior endplate 20. Engagement features such as projections or slots are formed along the outer edges to engage with the inner surfaces of the fingers 98. FIGS. 10 and 11 illustrate projections that can mate within slots 97 on the fingers 98.

The sled 71 also includes a base 72 with a threaded aperture 86 at the proximal end 76. The aperture 86 aligns with the channel 81 when the sled 71 is connected to the handle 90. The aperture 86 is threaded to engage with the screw 84 (or the threaded end of the member 82 depending upon the embodiment). A pair of ramps 74 are positioned towards the distal end 75. The ramps 74 include inferior and superior sides 78, 79 that angle away from each other towards the distal end 75. This orientation results in the height of the ramps 74 measured between the sides 78, 79 increasing towards the distal end 75. Projections 87 extend outward from some or each of the sides 78, 79 of the ramps 74. FIGS. 10 and 11 include a projection 87 extending outward from the inferior and superior sides 78, 79 of each of the ramps 74. The projections 87 may be structured as the projections 48 of the first member 41 described above. In one embodiment, the projections include a dovetailed shape.

Figure 12:
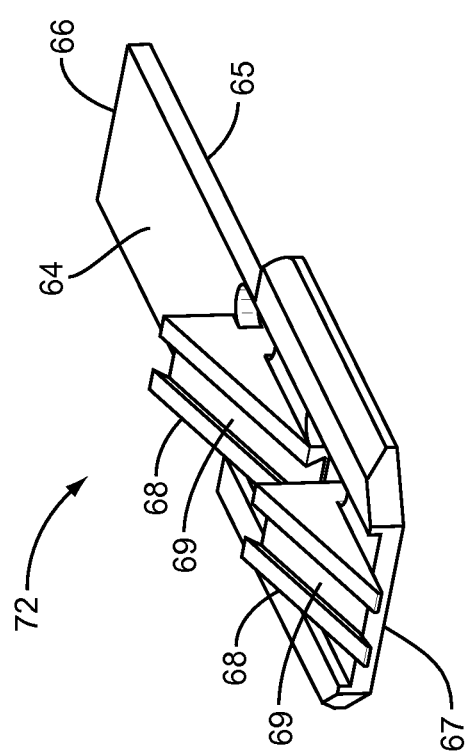
FIG. 12 is a perspective view of an interior side of a support according to one embodiment.

FIG. 12 includes a support 72 that engages with the sled 71. The distracter 70 includes a pair of supports 72 with a first support 72 on the superior side and a second support inferior side. The supports 72 may include the same or different shape, size, and configuration. The support 72 includes a proximal end 66 and a distal end 67. An interior side 64 faces towards the sled 71 and an exterior side 65 faces towards the plate 61. As illustrated in FIG. 8, the exterior side 65 includes a first section 31 and a second section 32. Each of the sections 31, 32 may be substantially planar with smooth surfaces. The first section 31 may be offset from the second section 32. The first section 31 may be configured to mate against the interior side 63 of the plate 61. The support 72 includes a width measured between lateral sides to fit within the central slot 25 on the interior side 22 of the endplates 20. The supports 72 are attached to the distal end of the ribbons 61. Specifically, the first section 31 is in contact with the interior side 63 of the ribbon 61 and may be connected in various manners, including welding, adhesives, and mechanical fasteners.

A pair of ramps 68 extends outward from the interior side 64. The ramps 68 include an inclined surface that increases in height from the distal end 67 towards the proximal end 66. This orientation causes the height of the ramps 68 to increase towards the proximal end 67. A slot 69 may be formed in the ramps 68. The slots 69 are configured to engage with the projections 87 on the sled ramps 74. FIG. 12 includes each of the ramps 68 formed by a pair of narrow inclined feature with the features being spaced apart a distance to form the slot 69.

Figure 13:
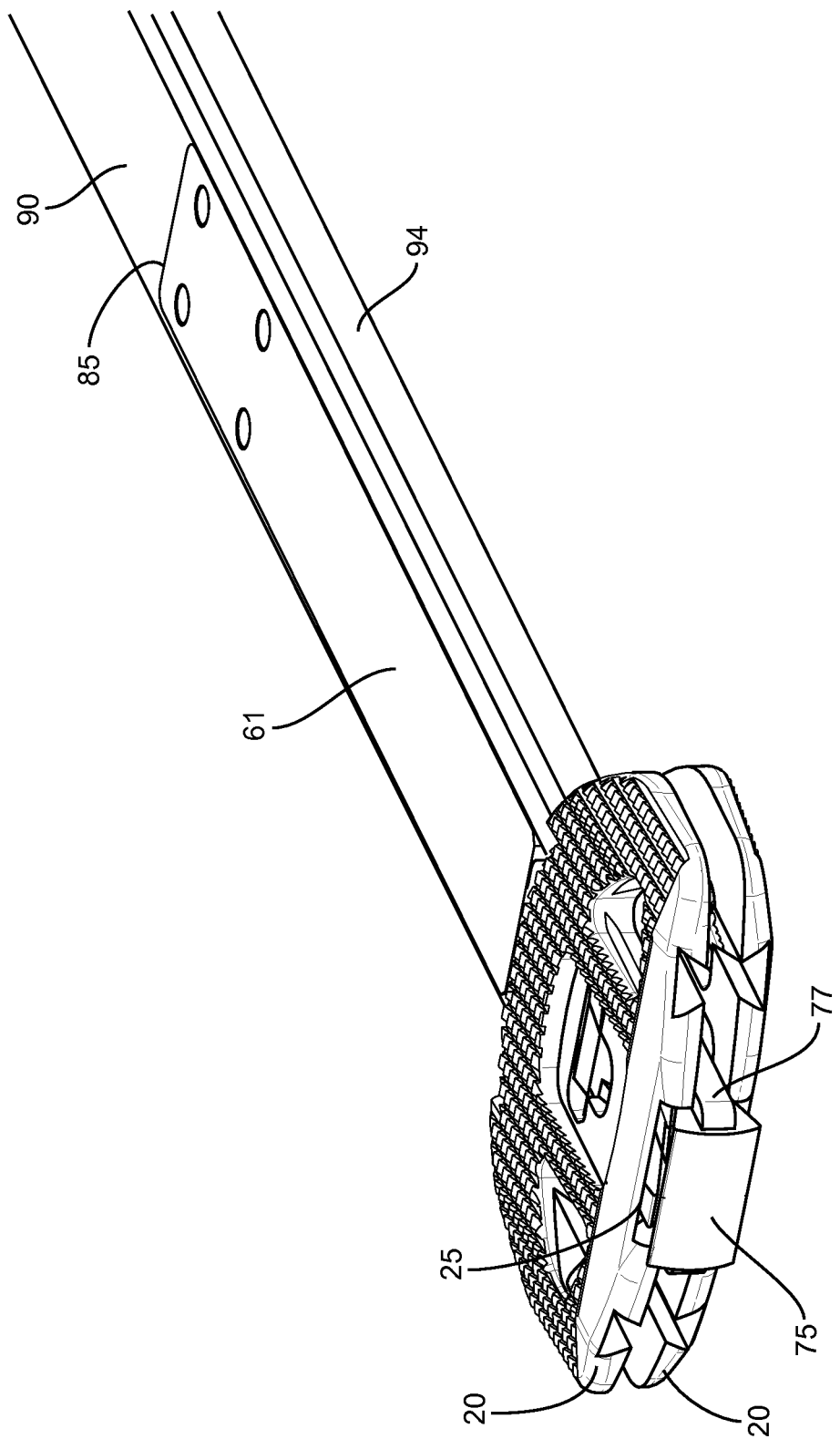
FIGS. 13-17 are perspective views of insertion and positioning of a modular interbody device into an intervertebral space using an insertion tool according to one embodiment.

FIGS. 13-17 illustrates the steps of inserting and deploying the device 100 within the intervertebral space 201. The vertebral members 200 are not included in these Figures for purposes of clarity. FIG. 13 includes the insertion tool 110 in an initial retracted orientation that has a reduced height. This includes the ramps 74 of the sled 71 being longitudinally offset from the ramps 68 of the supports 72. The interior sides 63 of proximal sections 32 of the ribbons 61 are positioned within the recesses 85 and connected to the handle 90 with mechanical fasteners. The connection may also be accomplished with adhesives, and welding. Because of the offset in height between the sections 31, 32 of the supports 72, the exterior sides 21 of the endplates 20 may be generally aligned with the exterior sides 62 of the ribbons 61. This relative positioning may provide for both these sides to contact the vertebral members 200 during the distraction process. Further, the distal ends of the ribbons 61 do not overlap with the endplates 20

The endplates 20 are positioned on the tool 110 with the interior side 22 facing the handle 90. The sled 71 and supports 72 are aligned within the central slot 25 on the interior side 22 of the endplates 20. The endplates 20 are positioned with the interior side 22 positioned over the second section 32 of the supports 72. Each of the endplates 20 is positioned on the tool 110, but the endplates 20 are not connected to each other. The endplates 20 are also positioned with the longitudinal axes of the engagement features aligned with the longitudinal axis of the tool 110.

The endplates 20 may be positioned on the handle 90 while the tool 110 is in a retracted or deployed orientation. However, prior to insertion into the intervertebral space 201, the tool 110 is in the retracted position. Further, the endplates 20 may be positioned at various locations along the length of the handle 90. The endplates 20 are usually positioned towards the distal end 91 as illustrated in FIG. 13 at the time of insertion into the intervertebral space 201.

After the endplates 20 are positioned, the surgeon manipulates the handle 90 and moves the endplates 20 into the intervertebral space 201. The rounded or tapered shape of the distal end 75 of the sled 71 transitions into the endplates 20 and facilitate the insertion process. At least the distal end 91 of the handle 90 and a portion of the distracter 70 are also positioned in the intervertebral space 201. The handle 90 is manipulated until the endplates 20 are properly positioned in the space 201. The length and width of the endplates 20 are fixed in size so the endplates 20 establish a footprint for the device 100 upon insertion into the space 201. The approach angle that the device 100 and tool 110 are inserted into the space 201 may vary. Approaches may include but are not limited to anterior, posterior, lateral, and oblique approaches.

Figure 14:
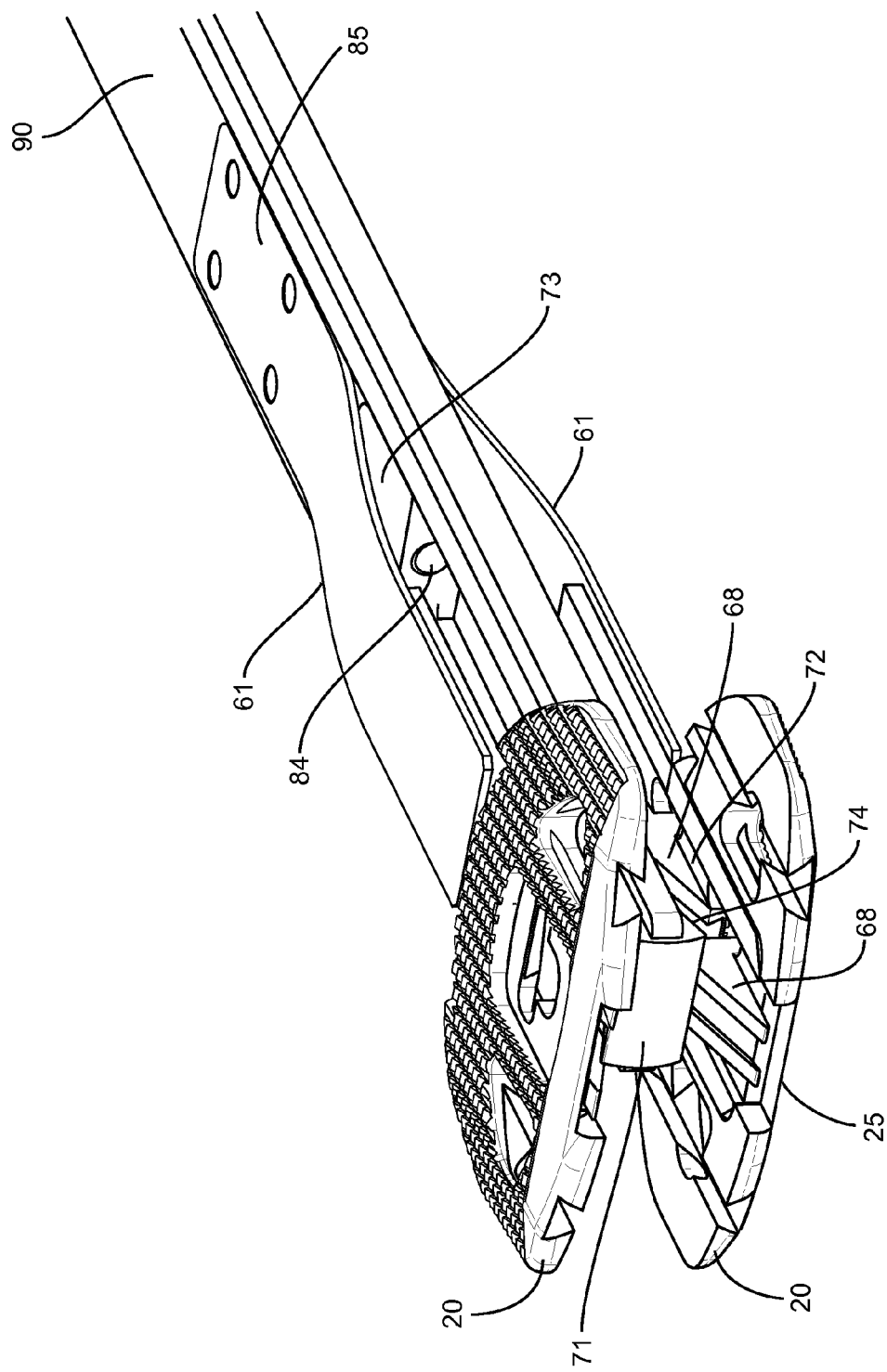

Once the endplates 20 are positioned in the intervertebral space 201, the tool 110 is deployed as illustrated in FIG. 14. The distraction occurs by the surgeon translating the member 82 relative to the body 93. This may occur by pulling the proximal end 92 that is attached to member 82 outward and away from the device 100 while the remainder of the insertion tool 110 remains relatively stationary. In one embodiment, an actuator tool 230 (FIGS. 8 and 18) is attached to the proximal end 92 to apply the force to the member 82. The tool 230 may include a dial that the surgeon rotates to apply the translational force. A height gauge 57 and a force gauge 58 may be associated with the proximal end 92 or the actuator tool 230. FIG. 8 illustrates the gauges 57, 58 on the actuator tool 230. The gauge 57 provides the surgeon with feedback to indicate the height H of the device 100, and gauge 58 indicates the force exerted by the device 100. The gauge 58 may determine the amount of torque being applied to the member 82.

In one embodiment, the height gauge 57 is operatively connected to the member 82. Rotation of the member 82 is indicated by the gauge 57 and corresponds to a particular height H of the device 100. Gauge 58 may also be operatively connected to the member 82. The gauges 57, 58 may both be part of the actuator tool 230 as illustrated in FIG. 8. Alternatively, one or both gauges 57, 58 may be part of the insertion tool 90. One embodiment includes both gauges 57, 58 being separate, although the functionality of the gauges may be combined into a single device. Further, a single gauge 57 or 58 may be included with the insertion tool 90 and the actuator tool 230. In one specific embodiment, the system includes just the height gauge 57. U.S. Pat. No. 7,087,055 discloses a distraction tool and is herein incorporated by reference in its entirety.

The translational movement causes the sled 71 to move within the pocket 96 along the longitudinal axis of the handle 90. Movement of the sled 71 causes the sled ramps 74 to slide along the support ramps 68. The inclined orientations of the ramps 74, 68 cause the height of the distracter 70 to increase. One or more gauges 57, 58 may be positioned on the exterior of the handle 90 or the actuator tool 230 to indicate the amount of translation and the corresponding increase in height of the device 100, and/or the distraction force. The surgeon may also determine the amount of distraction through tactile feedback they receive during the expansion of the device 100.

In the illustrated embodiment, the sled 71 moves in a proximal direction. The supports 72 are prevented from moving along the longitudinal axis of the tool because of contact and connection with the ribbons 61. The movement of the sled 71 relative to the longitudinally stationary supports 72 causes the supports 72 to move outward away from the body 93. This outward movement increases the distance between the opposing endplates 20. The force applied to the endplates 20 is transferred to the vertebral members 200 to distract the vertebral members 200.

The ribbons 61 are also moved outward away from the body 93. Because the ribbons 61 are attached to the body 93 of the handle 90 and the supports 72, the ribbons 61 bend to a curved configuration as illustrated in FIG. 14. In one embodiment, the ribbons 61 assume an "S" shape. The ribbons 61 may also contact against the vertebral members 200 and apply a distraction force.

Figure 15:
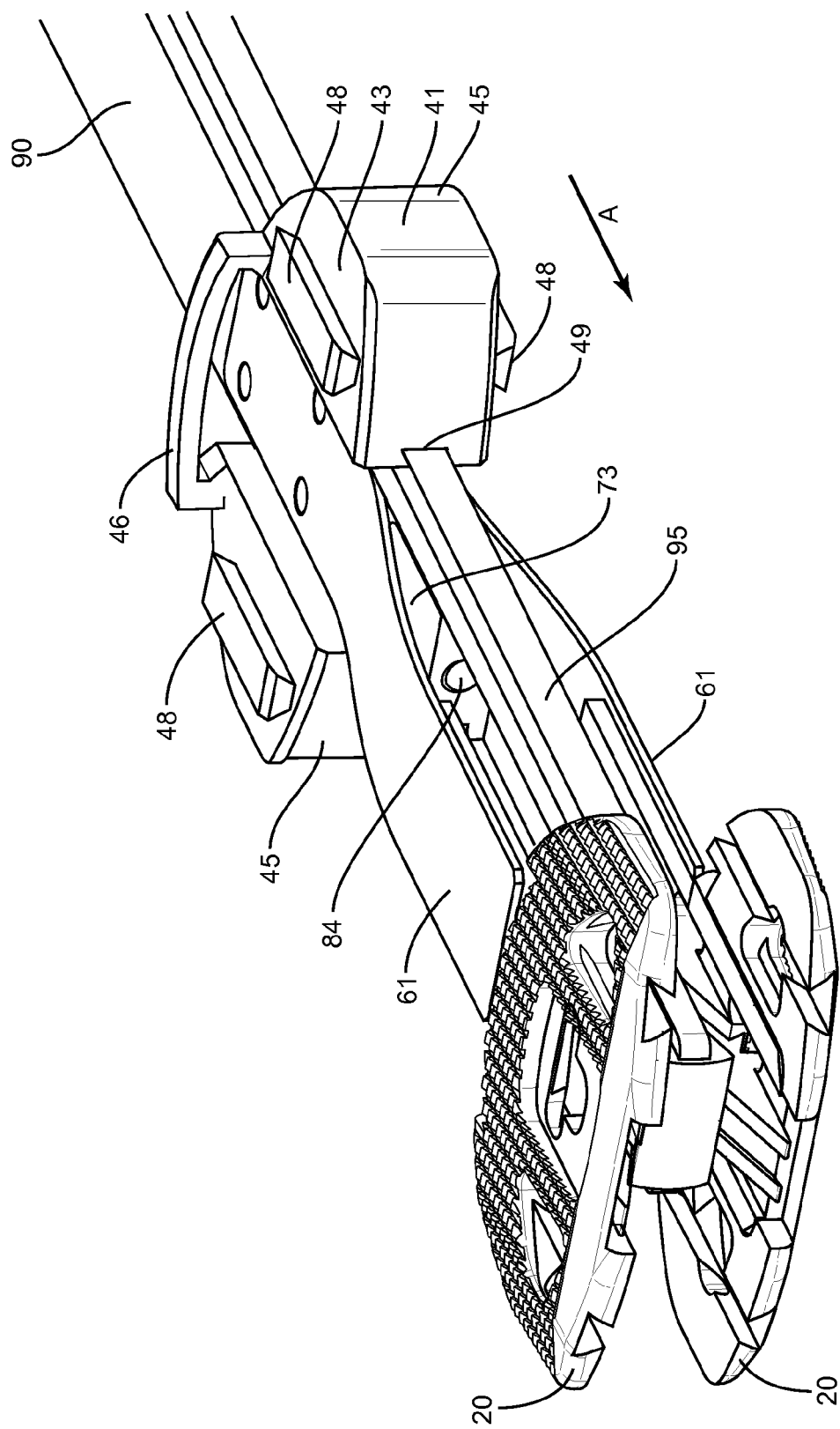

After the endplates 20 are separated to the desired height H, the intermediate section 40 is inserted between the endplates 20. As illustrated in FIG. 15, the first member 41 is moved along the handle 90 and between the endplates 20. The first member 41 may be connected to the handle 90 prior to the endplates 20. In one embodiment, prior to positioning the endplates 90 on the handle 90, the first member 41 is aligned with the distal end 91 of the handle 90. Slots 49 on the inner surfaces of the sections 45 are aligned with projections 95 on the sides 94 of the handle 90. The first member 41 is inserted onto the handle 90 with the slots 49 receiving the projections 95. The first member 41 is moved longitudinally along the length of the handle 90 towards the proximal end 92 and away from the distal end 91 such that it will not interfere with positioning the endplates 20 on the handle 90 and the distraction process.

Figure 16:
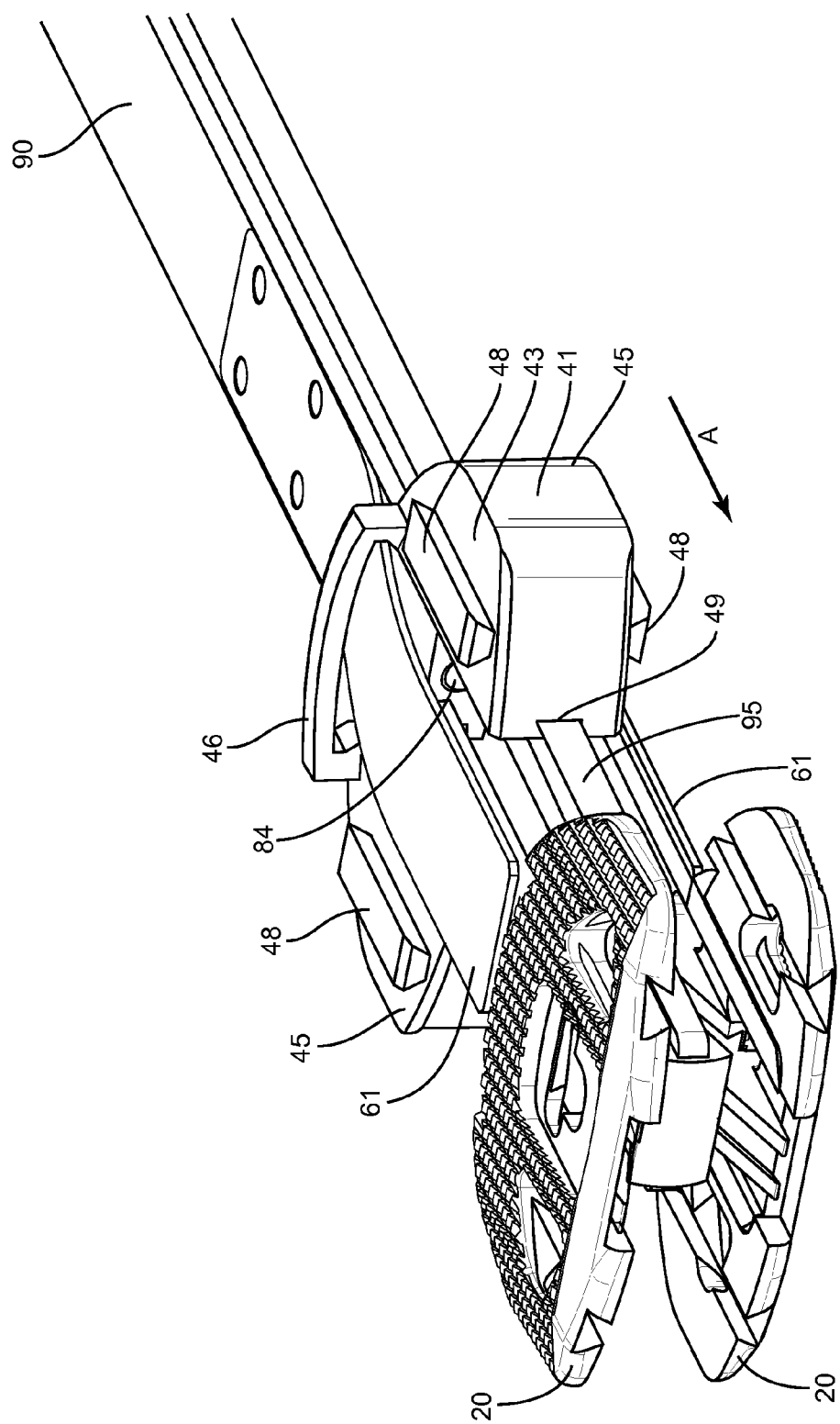

Returning to FIG. 15, the first member 41 is moved in the direction of arrow A along the length of the handle 90 and towards the spaced-apart endplates 20. In this embodiment, the slots 49 and projections 95 each include a dovetailed configuration to allow sliding of the first member 41 along the handle 90, and prevent detachment of the first member 41. The connector 46 of the first member 41 extends outward beyond the superior side 43 and extends over the exterior side 62 of the plate 61. FIG. 16 illustrates the first member 41 slid further along the handle 90 towards the endplates 20.

Figure 17:
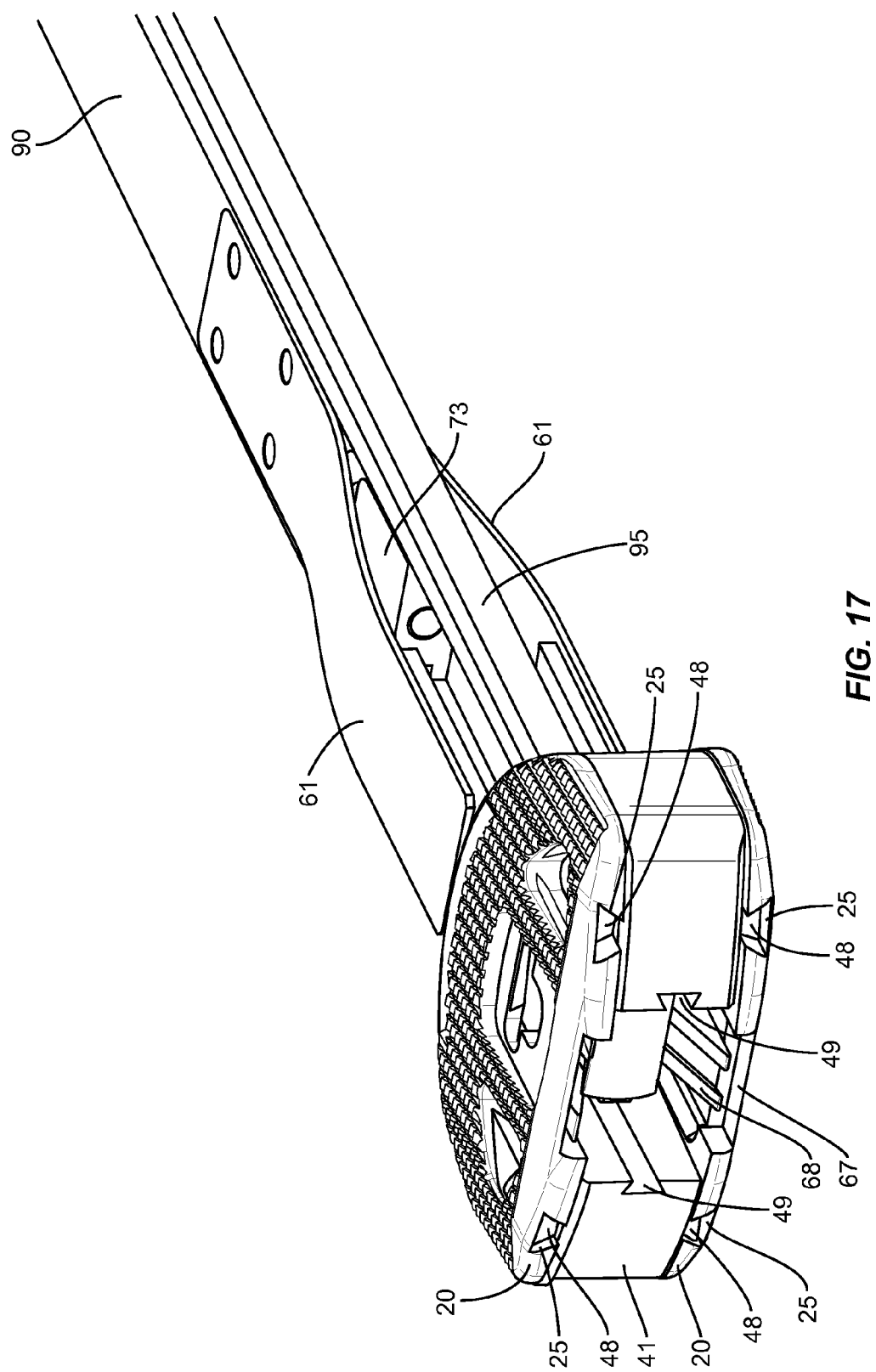

The first member 41 is further moved along the handle 90 and into engagement with the endplates 20. The engagement of the first member 41 may occur while at least a portion of the sled 71 and/or supports 72 remain within the intervertebral space 201 and the supports 72 are in contact with the endplates 20. The engagement features of both the endplates 20 and the first member 41 may be aligned to be parallel with the longitudinal axis of the handle 90. Therefore, these features engage together as the first member 41 is inserted between the endplates 20. Specifically as illustrated in FIG. 17, the projections 48 on the superior and inferior sides 43, 44 of the first member 41 slide into slots 25 in the interior sides 22 of the endplates 20.

The engagement features may include a locking structure to lock the first member 41 relative to the endplates 20 once fully inserted. The locking structures may include a first structure on the first member 41 that mates with a corresponding second structure on the endplates 20. Examples include a ball-and-detents, locking flanges and tabs, taper locks/snap fit, and the like. A secondary locking feature may also be used to connect the first member 41 to the endplates 20. Examples include adhesives, and mechanical fasteners.

Once the first member 41 is fully inserted, the insertion tool 110 may be removed. This may include moving the tool 110 back towards the retracted position by translating the member 82 in an opposite direction. This movement causes the sled 71 to move in an opposite direction relative to the supports 72 and decrease the height. Once decreased, the tool 110 may be removed from the intervertebral space 201. Alternatively, the tool 110 may be removed while in the expanded position.

In some embodiments, the completed device 100 includes the endplates 20 and the first member 41. The gap 47 in the first member 41 may be used to receive bone growth material to facilitate fusion to the vertebral members 200. Other embodiments include the second member 42 as illustrated in FIG. 7 inserted into the gap 47 in the first member 41. The surgeon may align the engagement features of the second member 42 with those on the first member 41 and then apply an insertion force insert the second member 42. Full insertion of the second member 42 may align the receptacle 55 with the apertures 24 in the endplates 20. Prior to insertion, bone growth material may be placed in the receptacle 55.

The insertion tool 110 may cause the endplates 20 to expand and remain parallel. The insertion tool 110 may also cause the endplates 20 to be expanded in a variable manner to accommodate the curvature of the spine and the dimensions of the intervertebral space 201. Further, the embodiments described above include the device 100 and the insertion tool 110 expanding a pair of endplates (i.e., both endplates 20 are moved away from the handle 90). Another embodiment may include the device 100 and/or insertion tool 110 moving only one of the endplates 20 as the other endplate 20 is relatively stationary.

Embodiments of the device 100 may include one or both endplates 20 with varying thicknesses in one or more planes. Alternatively, the intermediate section 40 may include one or more angled faces configured to position otherwise flat endplates 20 in a desired orientation.

The distraction mechanism described above includes a pair of ramped members. Another type of distraction mechanism includes a series of linkages attached to endplates. U.S. Pat. Nos. 7,087,055 and 7,070,598 and U.S. patent application Ser. No. 10/779,048 disclose various distraction mechanisms and are each herein incorporated by reference in their entireties. Other distraction mechanisms may include inflatable members positioned between opposing endplates, and rotating cam mechanisms positioned between the endplates.

The device 100 and insertion tool 110 may be used on various sections of the spine, including the cervical, thoracic, lumbar and/or sacral portions of the spine.

The surgical tool 110 may be made from any suitable materials, such as stainless steel, titanium, titanium alloys, or any other suitable materials known in the art. The device 100 may be made from materials including metals, plastics, polymers, ceramics, and others. The device 100 may also be made from a combination of different materials and coated with one or several materials. The endplates may have surface treatments such as the addition of bone growth promoting substances. In one embodiment, the various elements (e.g., endplates, first member, second member) may be made from different materials. In one specific embodiment, the endplates 20 are made from titanium, the first member 41 is made from PEEK, and the second member 42 is made from hydroxyapatite.

The various elements of the interbody device 100 and insertion instrument 110 may include a variety of different engagement features. Examples include but are not limited to slots and projections. The engagement features may vary among the interbody device 100 and insertion instrument 110. For example, the elements illustrated and described above with slots may include projections or other engagement features and the elements described with projections may include slots or other engagement features.

Figure 18:
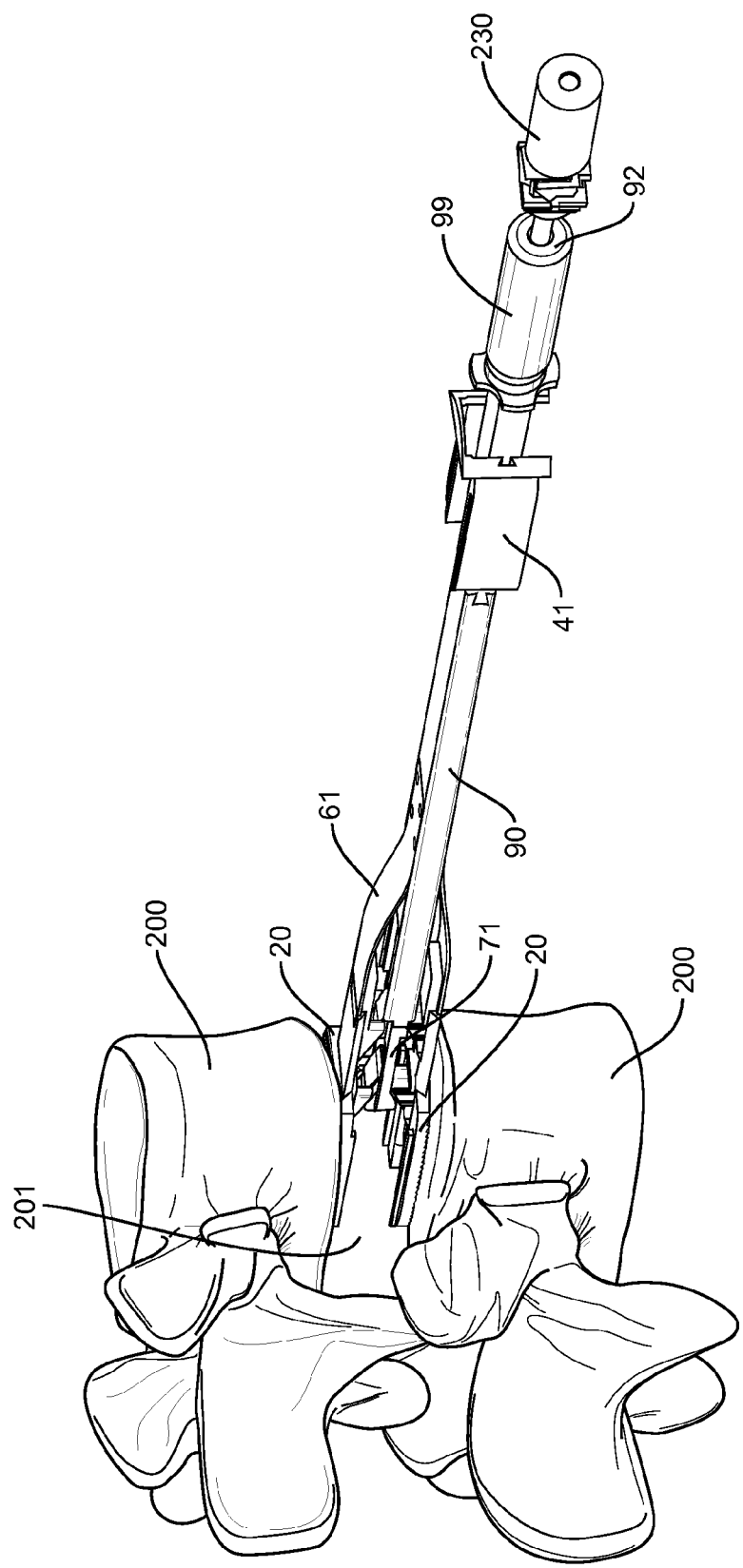
FIG. 18 is a perspective view of insertion and positioning of a modular interbody device into an intervertebral space with an insertion tool using a lateral approach according to one embodiment.

The embodiment described above in FIGS. 13-17 includes a device 100 configured for an anterior approach. The device 100 may also be configured for other approach angles. FIG. 18 includes an insertion process using a lateral approach for insertion of the device 100 into the intervertebral space 201. The endplates 20 include engagement features that extending in a lateral direction to engage with corresponding features on the insertion tool 110. Similarly, the intermediate section 40 (not illustrated) includes insertion features oriented in the same manner to engage with the endplates 20.

The implants 10 may be implanted within a living patient for the treatment of various spinal disorders. The implant 10 may also be implanted in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of inserting a modular interbody device into an intervertebral space between first and second vertebral members comprising:
    inserting a pair of endplates positioned on an elongated handle into the intervertebral space;
    deploying a distracter and increasing a distance between the endplates;
    bending a ribbon that connects the distracter to the handle while deploying the distracter such that the ribbon is in a bent configuration;
    contacting the ribbon against one of the first and second vertebral members when the ribbon is in the bent configuration;
    while the ribbon is bent, inserting an intermediate member between the endplates; and
    removing the handle from the endplates after inserting the intermediate member between the endplates.

2. The method of claim 1, further comprising orienting the distracter in a retracted position with the ribbon being straight prior to inserting the pair of endplates into the intervertebral space.

3. The method of claim 1, wherein the step of bending comprises bending the ribbon into a curved configuration while deploying the distracter.

4. The method of claim 1, wherein the step of bending comprises bending an intermediate section of the ribbon that is positioned between a distal section connected to the distracter and a proximal section connected to the handle.

5. The method of claim 1, after the step of inserting the intermediate member between the endplates, retracting the distracter and moving the ribbon to a straight orientation and then removing the distracter.

6. The method of claim 1, further comprising inserting a distal end of the ribbon into the intervertebral space and a proximal end away from the intervertebral space and guiding the intermediate section over the bent ribbon and between the endplates.

7. The method of claim 1, further comprising indicating a height of the device with a gauge positioned on the handle.

8. The method of claim 7, further comprising indicating a distraction force applied to the vertebral members.

9. A method of inserting a modular interbody device into an intervertebral space between first and second vertebral members comprising:
    inserting a pair of end members positioned on opposing sides of a lifting mechanism of a distracter into the intervertebral space with the distracter spacing apart the end members in a non-overlapping orientation, wherein ribbons connect the distracter to a handle;
    positioning the end members and the lifting mechanism in the intervertebral space relative to the first and second vertebral members;
    deploying the lifting mechanism and increasing the spacing between the end members while the lifting mechanism remains positioned in the intervertebral space;
    bending an intermediate section of at least one ribbon of the ribbons that is positioned between a distal section connected to the distracter and a proximal section connected to the handle;
    while said at least one ribbon is bent, inserting an intermediate member into the intervertebral space and between the end members while the lifting mechanism remains positioned in the intervertebral space and the end members remain spaced apart; and
    supporting the end members with the intermediate member and removing the lifting mechanism from the intervertebral space.

10. The method of claim 9, wherein the step of inserting the pair of end members comprises inserting the end members and the lifting mechanism into the intervertebral space using one of a lateral, anterior, posterior, and oblique approach.

11. The method of claim 9, wherein deploying the lifting mechanism and increasing the spacing between the end members while the lifting mechanism remains positioned in the intervertebral space includes moving a first ramped section of the lifting mechanism relative to a second ramped section of the lifting device.

12. The method of claim 11, further comprising moving a portion of the first ramped section out of the intervertebral space.

13. The method of claim 9, further comprising positioning a portion of the handle attached to the distracter into the intervertebral space while positioning the end members and the lifting mechanism in the intervertebral space relative to the first and second vertebral members.

14. The method of claim 9, further comprising contacting the end members with both the intermediate member and the lifting mechanism prior to removing the lifting mechanism from the intervertebral space.

15. The method of claim 9, further comprising inserting a second portion of the intermediate member between the end members.

16. The method of claim 9, further comprising contacting the end members against the first and second vertebral members and distracting the first and second vertebral members.

17. The method of claim 9, further comprising moving the intermediate member into contact with the end members and locking the intermediate member to the end members.

18. A method of inserting a modular interbody device into an intervertebral space between first and second vertebral members comprising:
    inserting a pair of end members connected to a distal end of an elongated handle into the intervertebral space while the end members are spaced apart a distance and out of contact with each other, wherein ribbons connect a distractor to the handle;

positioning the end members in the intervertebral space relative to the first and second vertebral members;

generating a distraction force within the intervertebral space and increasing the distance between the end members;

bending an intermediate section of at least one ribbon of the ribbons that is positioned between a distal section connected to the distracter and a proximal section connected to the handle;

while said at least one ribbon is bent, moving an intermediate member attached to the handle along the handle from a proximal section towards the distal end and into the space between the end members while the handle remains connected to the end members, the intermediate member including a first section positioned on a first side of the handle and a second section positioned on an opposing second side of the handle;

connecting together engagement features on the end members and the first and second sections of the intermediate member while the handle remains connected to the end members; and removing the handle from the end members.

19. The method of claim 18, further comprising moving the intermediate member over the distractor.

20. The method of claim 18, further comprising inserting a second intermediate member into the space between the end members.

21. A method of inserting a modular interbody device into an intervertebral space between first and second vertebral members comprising:

connecting an intermediate member to a distal end of an elongated handle with a first section of the intermediate member on a first side of the handle and a second section of the intermediate member on an opposing second side of the handle;

sliding the intermediate member along the handle away from the distal end;

positioning a first endplate on a superior side of the distal end of the handle and positioning a second endplate on an inferior side of the distal end of the handle with the endplates being spaced apart in a non-overlapping orientation;

inserting the first and second endplates and the distal end of the handle into the intervertebral space with the intermediate member spaced away from the intervertebral space;

expanding the distal end of the handle and moving the first and second endplates farther apart and into contact with the vertebral members;

after moving apart the first and second endplates and while the endplates are positioned on the distal end of the handle, sliding the intermediate member along the handle and between first and second endplates with elongated engagement features on the intermediate member engaging with corresponding elongated engagement features on the first and second endplates;

removing the distal end of the handle from the first and second endplates and the intermediate member; and supporting the endplates within the intervertebral space with the intermediate member.

\* \* \* \* \*